| United States Patent [19] | [11] Patent Number: 4,948,726 |
| --- | --- |
| Longoria | [45] Date of Patent: Aug. 14, 1990 |

[54] ENZYME IMMUNOASSAY BASED ON MEMBRANE SEPARATION OF ANTIGEN-ANTIBODY COMPLEXES

[76] Inventor: Claude C. Longoria, 2927 Field Line Dr., Sugar Land, Tex. 77479

[21] Appl. No.: 311,222

[22] Filed: Mar. 20, 1989

Related U.S. Application Data

[63] Continuation of Ser. No. 869,242, Jun. 2, 1986, abandoned.

[51] Int. Cl.$^5$ .............................................. G01N 33/53
[52] U.S. Cl. .......................................... 435/7; 435/14; 435/15; 435/18; 435/19; 435/21; 435/28; 436/536; 436/538; 436/541
[58] Field of Search ....................... 436/538, 536, 541; 435/7, 15, 18, 19, 21, 28

[56] References Cited

U.S. PATENT DOCUMENTS 4,517,288  5/1985  Giegel et al. ........................ 436/538

*Primary Examiner*—Sam Rosen
*Attorney, Agent, or Firm*—James L. Jackson

[57] ABSTRACT

An enzyme immunoassay based on membrane separation of antigen-antibody complexes wherein human or animal body fluid specimens containing an antigen are mixed with an enzyme-conjugated antibody specific for the antigen under test. Following incubation the antigen-antibody-conjugate mixture is passed through a filter membrane having an electrostatic charge providing an affinity for retaining antigen-antibody-conjugate complexes while not retaining free antibody-conjugate. Following washing of the filter membrane to remove free antibody-conjugate remaining thereon an enzyme substrate-chromogen reagent solution is applied to the filter membrane, which reacts with filter-bound antibody-conjugate and develops a visible or fluorogenic color indicative of the presence of antibody-conjugate.

34 Claims, No Drawings

ENZYME IMMUNOASSAY BASED ON MEMBRANE SEPARATION OF ANTIGEN-ANTIBODY COMPLEXES

This is a continuation of application Ser. No. 06/869,242 filed June 2, 1986, now abandoned.

FIELD OF THE INVENTION

This invention relates to methods for detecting and/or determining the concentration of antigens or antibodies in fluids. The invention relates generally to novel methods for performance of enzyme immunoassay (EIA) techniques, and to the separation of complexed reactants in particular. Another aspect of the invention relates to the use of a molecule such as avidin to increase the sensitivity and efficiency of the novel EIA techniques employed. This invention also relates to the use of these novel methods in immunoassay procedures for the quantitative and qualitative determination of various substances in body fluids such as urine, blood, serum, and saliva, and in carrier fluids in which the substance to be detected is suspended.

BACKGROUND OF THE INVENTION

For purposes of this invention, antigen is defined as a reactant from a group consisting of proteins, virus, cells, bacteria, parasites, antibodies and drugs.

Enzyme immunoassay (EIA) is a relatively new analytical technique that has found wide application for the determination of the presence of or concentration of antigenic substances associated with infectious disease, physiological condition, or drug monitoring. EIA techniques have been shown to provide high sensitivity, excellent specificity, and relative simplicity as compared to other immunoassay methods.

Generally, EIA employs the use of an enzyme labeled antibody conjugate directed against the antigen which is being detected or measured, and a primary antibody directed against the antigen. After appropriate incubation and separation procedures, measurement of the enzyme label by colorimetric, spectrophotometric or fluorometric techniques provides a simple and efficient method for detection and quantitation of the antigen.

A difficult and cumbersome problem in EIA methodology has been the separation of the reacted antibody conjugate from the unreacted antibody conjugate. During incubation of the antigen with the primary antibody and enzyme labeled antibody conjugate, a complex is formed by the common attachment of the antigen to the primary antibody and conjugate. Unreacted conjugate, including free and non-specifically bound conjugate must then be separated from the reacted complexed conjugate. After separation and removal of the unreacted conjugate, the antigen-bound enzyme labeled antibody conjugate is measured.

To facilitate the separation of bound from unbound reactants, most EIA techniques in the prior art describe enzyme-linked immunosorbent assays (ELISA). Common to ELISA techniques is the binding or attachment of the primary antibody to a solid-support component or material. The primary antibody is usually attached to a polymeric insoluble solid-support such as a plastic bead. After incubation with the antigen and the enzyme labeled antibody conjugate, the bead is subjected to various washing procedures to remove unreacted conjugate from the system. The bead is then exposed to a substrate for measurement of the bound enzyme conjugate.

A large number of solid-support materials and techniques for use of such materials have been described in the prior art. In one technique, described by Bohn, et al in the U.S. Pat. No. 4,424,279 small beads housed within a plunger device are coated with an antibody to form the solid phase. Deindoerfer, et al in U.S. Pat. No. 3,999,948 describes an antibody-coated solid support consisting of a polymeric film attached to a plastic holder with a handle to facilitate stirring and washing steps. Schall teaches in U.S. Pat. No. 4,363,634 a process for coating a glass support with a polymeric film, with subsequent attachment of an antibody to the film to yield a solid support for immunoassays. Other materials commonly used as solid support components include plastic tubes and microtiter plates, latex and glass particles, and silicone rubber.

The use of cellulose and glass fiber filters for solid support immunoassays has been described. Schutt describes in U.S. Pat. No. 4,357,311 a method for coupling antibody to a filter membrane solid support for use in immunoassay procedures. Katz, et al, in U.S. Pat. No. 4,496,654 describes the bonding of an antibody to an avidin coated paper disc with subsequent use of this paper disc as a solid support in an immunoassay.

Though the use of these solid supports facilitates the separation of reactants in EIA techniques, a number of disadvantages exist. Uniform adsorption of antibody to the solid-support material is required to achieve reproducibility and sensitivity. The ionic charge of the solid support material must be critically controlled to ensure efficient and reproducible adsorption. Numerous problems have been encountered due to lot-to-lot variation in adsorptive characteristics of plastic resins. Antibody adsorbed to these materials is gradually lost from the support surface during the incubation and wash steps, thus reducing the sensitivity of the assay. Non-specific adsorption of the antigen and/or enzyme labeled antibody to the solid-support during incubation may reduce the specificity of the assay.

The use of reactants bound to a solid phase may require long antigen-antibody incubation periods due to inefficient reaction kinetics when one or both reactants are not distributed uniformly throughout the reaction solution. Additionally, steric hindrance may result in less efficient antigen-antibody binding when the reactants are attached to a polymeric support.

Washing procedures employed in ELISA methods are often messy, cumbersome and time-consuming and may be too complicated to be performed in a clinical laboratory. Wash procedures generally involve pouring-off or aspiration of incubation fluids from tubes or microtiter plates followed by addition and removal of copious volumes of wash buffer.

Procedures involving plastic, glass or latex beads may require centrifugation of the incubation fluid followed by removal of supernatants and several additional centrifugation-wash steps. "Dipstick" tests which feature a solid-support material attached to a plastic strip or holder often require moving the test strip sequentially to various tubes of buffer; or, such tests may require rinsing under running tap water for various time intervals.

The present invention overcomes these disadvantages through the use of a novel reactant separation technique which does not require the use of a solid-support or solid phase component.

SUMMARY OF THE INVENTION

An enzyme immunoassay (EIA) technique which utilizes membrane filters having unique biochemical and ionic characteristics for the separation of free and complexed reactants. This EIA technique involves the use of electrostatically charged filters to trap or adsorb antigen-antibody complexes as a means of separating the free from the bound reactants. An antibody or antigen immobilized on a solid-support material is not required as a component of the test. The separation of reactants is accomplished after incubation by filtration or diffusion of the fluid through a specially formulated filter paper followed by minimal volumes of wash buffer. The EIA technique may be performed on automated or single-use disposable filter devices and results may be read visually, spectrophotometrically or electronically. Various methods may be employed to increase the efficiency and sensitivity of the technique.

DESCRIPTION OF THE PREFERRED EMBODIMENTS

The EIA methodology of the current invention is based on the unexpected discovery that antigen-antibody complexes exhibit a unique and distinctive net ionic charge differing from the ionic charge of each of the individual reactant antigen and antibody molecules. It was further discovered that such antigen-antibody complexes could be retained by passage of the carrier fluid through a filter paper matrix having an electrostatic affinity for such complexes while having minimal or lesser affinity for un-complexed antigen and antibody molecules. Further work demonstrated that these ionic characteristics had practical application as a means of separating complexed molecules from unbound molecules in an EIA procedure without the need for a solid-phase support.

The basic immunological reaction for the detection of antigen (e.g. in infectious disease), in an exemplary form, is described as follows. The fluid specimen containing the antigen is mixed with enzyme-conjugated antibody specific for the antigen under test. After a short incubation period, the fluid mixture is passed through a filter membrane using positive or negative pressure, or diffusion. The filter is formulated to electrostatically retain the antigen-antibody-conjugate complexes while free antigen or antibody-conjugate passes through the filter or diffuses away from the inoculation site. In the case of particulate antigens such as cells, bacteria or parasites, the antigen, with or without antibody-conjugate attached, can be retained using a filter formulated to retain particulates by electrostatic charge and/or physical entrapment. The filter is washed by passing a small volume of wash solution through. The wash solution serves to remove free enzyme or conjugate which may be non-specifically retained on the filter; thus conjugate or enzyme which remains on the filter after washing represents reactants which have complexed with the antigen. A substrate-chromogen solution is then applied to the filter or passed through the filter. The substrate-chromogen solution reacts with filter-bound conjugate and color development (visible or fluorogenic) occurs on the membrane.

The basic immunological reaction for the detection of antibody, in an exemplary form, is described as follows. The fluid specimen containing the antibody is mixed with enzyme-conjugated antigen. After a short incubation period, the fluid mixture is passed through a filter membrane using positive or negative pressure, or diffusion. The filter is formulated to electrostatically retain the antibody-antigen-conjugate complexes while free antibody or antigen-conjugate passes through the filter or diffuses away from the inoculation site. The filter is washed by passing a small volume of wash solution through. The wash solution serves to remove free enzyme or conjugate which may be non-specifically retained on the filter; thus conjugate or enzyme which remains on the filter after washing represents reactants which have complexed with the specific antibody. A substrate-chromogen solution is then applied to the filter or passed through the filter. The substrate-chromogen solution reacts with filter-bound conjugate and color development (visible or fluorogenic) occurs on the membrane.

The summary above and the following explanations and examples are intended only to demonstrate the usefulness and wide application of the current invention and are not to be taken in a limiting sense. It is understood that numerous other adaptations and applications may be made within the scope of the current invention. As in other EIA techniques, various modifications in procedure can be made, with the common aspect of this novel process being the ability to utilize a filter paper which preferentially binds or adsorbs antigen-antibody complex while allowing the individual, un-complexed reactants to pass through. This allows a simple, rapid and efficient separation technique which offers numerous advantages over existing methods which utilize a solid support and require elaborate washing procedures to separate the complexed reactants from the un-complexed reactants.

A competitive procedure for detection of antigen may be performed by incubating unlabeled antibody specific for the antigen under test and a standard enzyme labeled antigen with the test fluid. Antigen present in the test fluid competes with the standard enzyme labeled antigen for the available antibody sites. After appropriate filtration and wash procedures, a reduction in enzyme activity as compared to a standard control indicates the presence and quantitation of the test antigen.

The reagents and biological molecules employed in the current invention are those common to EIA techniques. The enzyme label may be selected from the group consisting of alkaline phosphatase, acid phosphatase, glucose oxidase, beta-galactosidase, beta-lactamase, urease or horseradish peroxidase. The preferred enzymes are alkaline phosphatase and horseradish peroxidase. A number of enzyme substrate/chromogen reagents are available, with the most preferred selected from the group consisting of:

p-nitrophenyl-phosphate (PNPP)
5-bromo-4-chloro-3-indolyl-phosphate (BCIP)
4-Methylumbelliferyl phosphate (MUP)
Hydrogen peroxide or organic peroxide substrate with the following chromogens:
3-amino-9-ethylcarbazole (AEC)
3,3-diaminobenzidine (DAB)
2,2'-azino-di (3-ethylbenzthiazoline sulfonic acid) (ABTS)
o-phenylenediamine (OPD)
3-3',5,5'-tetramethyl benzidine (TMB)

Antibody reagents typically employed in the current invention are IgG or IgM antibodies produced in rabbits, or goats and affinity-purified. Alternatively, monoclonal antibodies may be used and may offer the advantage of providing greater specificity. Enzyme conjugates are typically prepared using modifications of the procedures outlined by Nakane, et al and Voller, et al. Conjugates are stabilized by addition of agents (e.g. glycerol) which reduce the incidence of non-specific protein aggregation.

Buffers and wash reagents employed in the current invention are selected for optimum performance with the enzyme, substrate and filter paper system in use and buffering agents are usually selected from the group consisting of phosphate, tris, glycine, citric acid, and sodium acetate. Depending on the particular application, buffers may range in molarity from about 0.001 M to about O.3 M and may range in pH from about pH 3.5 to about pH 10. Buffers and wash reagents may contain blocking or coating proteins (e.g., Bovine Serum Albumin, Normal Serum or Gelatin) and surfactants (e.g., Tween 20, Tween 80, Triton X-100) to reduce non-specific adsorption of antibody conjugate to the filter paper. Triton X-100 is one of a number of a number of polyoxyethylene ether surfactants of Rhom and Haas % Co. Tween-20 is polyoxyethylenesorbitan monolaurate while Tween-80 is polyoxyethylene sorbitan monooleate.

Filter paper employed in the current invention is formulated and manufactured to critical standards for use in the EIA assays described herein. Filters usually are composed of cellulose or fiberglass and incorporate various fillers and binders to ensure control of pore size, electrostatic charge and hydrostatic characteristics. Depending on the particular application, the filter paper may exhibit a pore size in the range from about 0.2 microns to about 25 microns. Depending on the particular application, the electrostatic charge of the filter may vary in the range from strongly negatively charged to slightly positively charged. The majority of applications require a filter exhibiting a slight negative or net neutral charge.

After separation of the antigen-antibody complex from the unreacted components by filtration, the quantity of bound enzyme remaining on the filter is directly related to the quantity of analyte (antigen or antibody under test) originally present in the test fluid. The current invention provides for interpretation of results by either of two methods described below.

The substrate/chromogen may be added directly to the filter paper. As the retained enzyme reacts with the substrate/chromogen solution, color development or fluorescence occurs on the filter paper. The resulting color intensity may be compared visually to a color guide for a qualitative or semi-quantitative interpretation. Alternatively, the resulting color intensity or fluorescence may be measured through electronic means by density or reflectance photometry yielding a quantitative interpretation.

As an alternative to the addition of substrate/chromogen directly to the filter matrix, the bound enzyme or antigen-antibody-enzyme complex may be eluted from the filter paper. This elution is performed by the passage through the filter paper of a dissociation agent such as pH 10 buffer. The eluate containing the eluted enzyme is then collected and assayed for enzyme activity by neutralization and addition of substrate/chromogen solution. As the enzyme reacts with the substrate/chromogen solution, color development occurs in the eluate solution. The resulting color intensity is measured spectrophotometrically to yield a quantitative interpretation.

An improved method which allows for increased sensitivity employs substances in the form of a capture molecule and a target molecule exhibiting a natural binding affinity, such as the biological molecules avidin and biotin, to increase the efficiency of complex binding to the filter. Avidin and biotin are naturally occurring substances, chemical molecules, which have the unique property of binding very tightly to one another on a molecular level to form an extremely stable complex. The avidin-biotin system has been used in several diagnostic tests including U.S. patent application, Ser. No. 4,496,654 in which an avidin coating on a solid support was used to attach an antibody to the solid support in a diagnostic test for HCG (pregnancy test).

An affinity system employing a capture molecule and a target molecule such as the avidin-biotin system may be used in this novel EIA system as follows. Avidin is a protein which exhibits a very high isoelectric point. Therefore, it is very strongly positively charged at or near neutral pH. A filter paper exhibiting a net negative charge which has a high affinity for binding avidin, while having a very low affinity for binding enzyme-labeled antibody, is utilized to effect separation of the complex from the unreacted components.

The following examples are illustrative of the usefulness of the current invention and are not intended in a limiting sense. It is understood that various modifications may be made to the stated examples within the scope of the current invention.

EXAMPLE 1

RAPID QUANTITATION OF IgG IN HUMAN SERUM

Human serum is diluted 1:5000 in 0.03 M TT (Tris-HCl buffer, tris (hydroxymethyl) aminomethane, containing 0.05% Tween 20), pH 7.2. Alkaline Phosphatase (AP)-labeled affinity purified rabbit anti-human-IgG is diluted 1:500 in TT. A 0.3 ml volume of labeled antibody is added to 2.7 ml dilute human serum. The solution is vortexed to mix well. The solution is immediately passed through a 0.375" diameter filter (Product Code #186P, Applied PolyTechnology (APT), Inc.) under vacuum. After the solution has passed through the filter, 3.0 ml TT wash solution is passed through the filter. This wash is repeated two times. Eluent solution, 3.0 ml pH 10 Tris is added to the filter, passed through, and collected in a test tube. The eluate is neutralized and 0.5 ml PNP (1.0 mg/ml) is added to the eluate solution. The chromogen is allowed to ripen for 10 minutes. The color intensity of the solution is then measured in a spectrophotometer at 410 nm.

The above procedure was performed using dilutions of human serum containing known concentrations of IgG, and a standard nomograph was obtained. The absorbances obtained are listed below:

| Concentration of IgG (ug/ml) | Absorbance (@ 410 nm) |
| --- | --- |
| 0.53 | .945 |
| 0.26 | .538 |
| 0.13 | .323 |
| 0.07 | .177 |
| 0.03 | .106 |
| 0.01 | .038 |

| Concentration of IgG (ug/ml) | Absorbance (@ 410 nm) |
|---|---|
| 0.00 | .000 |

An unknown sample may be processed as described above and the resulting absorbance reading compared to the standard nomograph for a quantitative determination of IgG.

EXAMPLE 2

RAPID DETECTION OF PLATELET-ASSOCIATED IgG

Thrombocytopenia purpura is a platelet disorder in which there is a production of an IgG capable of reacting with the host's platelets, with subsequent destruction of platelets by the reticuloendothelial system. Following is a rapid method for detection of platelet-associated IgG.

Whole blood (0.1 ml) is lysed and centrifuged to isolate platelets. Suspend platelets in 0.05 M glycine buffer, pH 0 4 and filter through filter paper (PC #186, APT, Inc.). AP-labeled affinity purified rabbit anti-human-IgG is diluted 1:5000 in TT. A 3.0 ml volume of labeled antibody is passed through the filter paper under vacuum. Wash the filter three times by filtering 3.0 ml volumes of TT. Eluent solution, 3.0 ml pH 10 Tris, is added to the filter, passed through, and collected in a test tube. The eluate is neutralized and 0.3 ml PNP (1.0 mg/ml) is added to the eluate solution. The chromogen is allowed to ripen for 10 minutes. The color intensity of the solution is then measured in a spectrophotometer at 410 nm. An absorbance reading of greater than 0.100 indicates the presence of Platelet-associated IgG. Comparison of the above procedure to conventional, more time-consuming techniques indicated excellent correlation.

EXAMPLE 3

DETECTION OF STREPTOCOCCUS (GROUP A) FROM THROAT SWABS

Throat swab containing Group A Streptococcus bacteria is placed into a test tube containing 0.20 ml TTB buffer (0.03 M Tris-HCl+0.05% Tween 20+1.0% BSA). Press swab against inner surface of tube to expel fluid, remove and discard swab. Add 0.1 ml Horseradish Peroxidase (HRPO)-labeled affinity purified Anti-Group A Strep IgG (diluted 1:500 in TTB buffer). Incubate solution 10 minutes at room temperature Add fluid to well of disposable filter device and allow fluid to diffuse into filter (filter paper PC #413, APT, Inc.). After fluid has diffused into filter paper, wash three times by addition of 0.15 ml TTB buffer to well. After final wash has diffused into paper, add 0.1 ml TMBHP (0.03% TMB+0.03% hydrogen peroxide) substrate to orifice of filter disk. Development of a blue color on the filter paper within 3 minutes indicates the presence of Group A Strep bacteria. Lack of color development within a 3 minute period is indicative of a negative result. This method has been shown to correlate well with conventional culture methods.

EXAMPLE 4

TEST FOR PREGNANCY

A freshly voided urine specimen may be tested for pregnancy by addition of 0.1 ml urine to a test tube or reaction vessel containing 0.2 ml HRPO-labeled Anti-beta-HCG antibody (1:500) in PTB (0.05 M Phosphate buffer+0.05% Tween 20+0.05% BSA). After incubation for 20 minutes at room temperature, the fluid mixture is added to the well of the disposable filter disk and allowed to diffuse into the filter paper (PC#413P, APT, Inc.). The filter is washed three times by the addition of 0.15 ml PTB buffer. After the final wash, 0.1 ml TMBHP is added to the filter disk. Development of a blue color on the filter disk within 3 minutes indicates the presence of beta-HCG, i.e., a positive pregnancy test. Lack of color development indicates a negative pregnancy test. The sensitivity of the method is 75-125 mIU HCG/ml of urine.

EXAMPLE 5

RAPID TEST FOR PREGNANCY

A rapid and more sensitive pregnancy test may be performed using an affinity system as follows:

Add 0.1 ml urine to a test tube or reaction vessel containing the following reactants in PTB: (a) 0.2 ml HRPO-labeled Anti-beta-HCG antibody (1:500), (b) 0.1 ml Biotinylated Anti-beta-HCG (1:500), (c) 0.05 ml Avidin (0.1 mg/ml). After incubation for 3 minutes at room temperature, the fluid mixture is added to the well of the disposable filter disk and allowed to diffuse into the filter paper (PC #413P, APT, Inc.) The filter is washed three times by the addition of 0.15 ml PTB buffer. After the final wash, 0.1 ml TMBHP is added to the filter disk. Development of a blue color on the filter disk within 3 minutes indicates the presence of beta-HCG, i.e., a positive pregnancy test. Lack of color development indicates a negative pregnancy test. The sensitivity of the method is 30-50 mIU HCG/ml of urine.

What is claimed is:

1. An enzyme immunoassay process for detection of antigen based on membrane separation of antigen-antibody complexes, comprising:
   (a) mixing a fluid specimen containing the antigen with an enzyme-conjugated antibody specific for the antigen under test and forming an antigen antibody-conjugate having a distinctive net ionic charge differing from the ionic charge of each of the reactant antigen and antibody molecules;
   (b) retaining the antigen-antibody-conjugate mixture for a period sufficient for reaction of the antigen and antibody;
   (c) passing the reacted antigen-antibody-conjugate mixture through a filter membrane having a net electrostatic charge providing an affinity for retaining by adsorption thereto antigen-antibody-conjugate complexes having said distinctive net ionic charge while not having an electrostatic affinity for retaining free antibody-conjugate and permitting free antibody-conjugate to pass therethrough;
   (d) applying a wash solution to said filter membrane to remove free antibody-conjugate remaining thereon thus leaving antigen-antibody-conjugate electrostatically adsorbed by said filter membrane; and
   (e) applying an enzyme substrate-chromogen reagent solution to said filter membrane which reacts with filter-bound antigen-antibody-conjugate complex and develops a color indicative of the presence of said antigen-antibody-conjugate complex, said color being visible or fluorogenic.

2. An enzyme immunoassay process as recited in claim 1, wherein:
said enzyme-conjugated antibody comprises an enzyme from a group consisting of alkaline phosphatase, acid phosphatase, glucose oxidase, beta-galactosidase, beta-lactamase, urease and horseradish peroxidase.

3. An enzyme immunoassay process as recited in claim 1, wherein:
said enzyme substrate/chromogen reagent is from a group consisting of p-nitrophenyl-phosphate, 5-bromo-4-chloro-3-indolyl-phosphate, 4-methylumbelliferyl phosphate, hydrogen peroxide and organic peroxide substrate.

4. An enzyme immunoassay process as recited in claim 1, wherein:
said enzyme substrate/chromogen reagent includes chromogens from a group consisting of 3-amino-9-ethylcarbazole, 3,3-diaminobenzidine, 2,2'-azino-di-(3-ethylbenzthiazoline sulfonic acid), o-phenylenediamine, and 3,3',5,5' tetramethylbenzidine.

5. An enzyme immunoassay process as recited in claim 1, wherein:
said antibody reagent is from a group consisting of affinity-purified IgG antibodies, affinity purified IgM antibodies and monoclonal antibodies.

6. An enzyme immunoassay process as recited in claim 5, wherein:
said IgG antibodies and said IgM antibodies are produced in goats or rabbits.

7. An enzyme immunoassay process as recited in claim 1, including:
stabilizing said conjugates by addition of glycerol thereto for reducing the incidence of non-specific protein aggregation.

8. An enzyme immunoassay process as recited in claim 1, wherein:
a buffering agent is mixed with said fluid specimen and said enzyme-conjugated antibody and is selected from the group consisting of phosphate, tris, glycine, citric acid and sodium acetate.

9. An enzyme immunoassay process as recited in claim 8, wherein:
said buffering agent ranges in molarity from about 0.001 M to about 0.3 M.

10. An enzyme immunoassay process as recited in claim 8, wherein:
said buffering agent ranges in pH from about pH 3.5 to about pH 10.

11. An enzyme immunoassay process as recited in claim 8, wherein:
said buffering agent contains blocking and coating proteins from a group consisting of bovine serum albumin, normal serum and gelatin and said buffering agent contains a surfactant.

12. An enzyme immunoassay process as recited in claim 11, wherein:
said surfactant is from a group consisting of Tween 20, Tween 80 and Triton.

13. An enzyme immunoassay process as recited in claim 1, wherein:
said filter membrane is composed of a group consisting of cellulose, fiberglass, filled cellulose, filled fiberglass capable of sustaining a predetermined electrostatic charge and having a pore size in the range of from about 0.2 microns to about 25 microns.

14. An enzyme immunoassay process as recited in claim 13, wherein:
said predetermined electrostatic charge is in the range of from strongly negatively charged to slightly positively charged.

15. An enzyme immunoassay process as recited in claim 1, wherein:
intensity of said color is compared visually to reference colors for qualitative and semi-quantitative interpretation.

16. An enzyme immunoassay process as recited in claim 15, wherein:
the intensity or fluoresence of said color is measured by density or reflectance photometry, yielding quantitative interpretation.

17. An enzyme immunoassay process for detection of antigen, based on membrane separation of antigen-antibody complexes, comprising:
(a) mixing a fluid specimen containing the antigen with an enzyme-conjugated antibody specific for the antigen under test to form an antigen-antibody-conjugate mixture having a distinctive ionic charge;
(b) retaining the antigen-antibody-conjugate mixture for a period sufficient for reaction of the antigen and antibody;
(c) passing the reacted antigen-antibody-conjugate mixture through a filter membrane having a net electrostatic charge providing an electrostatic affinity for adsorption of antigen-antibody-conjugate complexes while not having an electrostatic affinity for adsorption of free antibody-conjugate;
(d) applying a wash solution to said filter membrane to remove free antibody-conjugate remaining thereon thus leaving antigen-antibody-conjugate electrostatically retained by said filter membrane;
(e) eluting the bound enzyme or antigen-antibody-enzyme complex from said filter membrane with a dissociation agent;
(f) collecting and assaying the eluate containing the eluted enzyme for enzyme activity by addition of substrate/chromogen solution thereto, said enzyme reacting with said substrate/chromogen solution and developing a color; and
(g) measuring the color intensity of said eluted enzyme spectrophotometrically to yield a quantitative interpretation.

18. An enzyme immunoassay process for detection of antibody based on membrane separation of antigen-antibody complexes, comprising:
(a) mixing a human or animal body fluid specimen containing the antibody with an enzyme-conjugated antigen specific for the antibody under test to form an antibody-antigen-conjugate mixture having a distinctive ionic charge;
(b) retaining the antibody-antigen-conjugate mixture for a period sufficient for reaction of the antigen and antibody to form a mixture having antibody-antigen-conjugate therein;
(c) passing the reacted antigen-conjugate mixture through a filter membrane having a net electrostatic charge providing an electrostatic affinity for retaining by adsorption antibody-antigen-conjugate complexes while not having a net electrostatic affinity for adsorption of free antigen-conjugate;

(d) applying a wash solution to said filter membrane to remove free antigen-conjugate remaining thereon, leaving antibody-antigen-conjugate electrostatically adsorbed to said filter membrane; and (e) applying an enzyme substrate-chromogen reagent solution to said filter membrane which reacts with filter-bound antibody-antigen-conjugate and develops a color indication of the presence of antibody-antigen-conjugate, said color being visible or fluorogenic.

19. An enzyme immunoassay process for detection of antigen, based on membrane separation of antigen-antibody complexes through the use of a molecular affinity capture system, comprising:

(a) mixing a fluid specimen containing the antigen with an enzyme-conjugated antibody specific for the antigen under test, a target-labeled antibody specific for the antigen under test and capture molecules specific for said target-labeled antibody and forming an antigen-conjugate-target-antibody capture molecule mixture having a distinctive ionic charge;

(b) retaining the antigen-conjugate-target-anti-body-capture molecule mixture for a period of time sufficient for reaction;

(c) passing the reacted antigen-conjugate-target-antibody-capture molecule mixture through a filter membrane having a net electrostatic charge providing an affinity for retaining by electrostatic adsorption said capture molecule while not having an electrostatic affinity for adsorption of free enzyme-conjugated antibody;

(d) applying a wash solution to said filter membrane to remove free enzyme-conjugated antibody remaining thereon thus leaving antigen-conjugate-target-antibody capture molecule mixture electrostatically adsorbed to said filter membrane; and (e) applying an enzyme substrate-chromogen reagent solution to said filter membrane which reacts with filter-bound enzyme-conjugated-antibody and develops a color indicative of the presence of said enzyme-conjugated-antibody, said color being visible or fluorogenic.

20. An enzyme immunoassay process as recited in claim 19, wherein:
said enzyme substrate/chromogen reagent is from a group consisting of p-nitrophenyl-phosphate, 5-bromo-4-chloro-3-indolyl-phosphate, 4-methylumbelliferyl phosphate, hydrogen peroxide and organic peroxide substrate.

21. An enzyme immunoassay process as recited in claim 19, wherein:
said enzyme substrate/chromogen reagent group includes chromogens from a group consisting of 3-amino-9-ethylcarbazole, 3,3-diaminobenzidine, 2,2'-azino-di-(3-ethylbenzthiazoline sulfonic acid), o-phenylenediamine, and 3,3',5,5' tetramethylbenzidine.

22. An enzyme immunoassay process as recited in claim 19, wherein:
said antibody reagent is from a group consisting of affinity-purified IgG antibodies, affinity purified IgM antibodies and monoclonal antibodies.

23. An enzyme immunoassay process as recited in claim 22, wherein:
said IgG antibodies and said IgM antibodies are produced in goats or rabbits.

24. The enzyme immunoassay process of claim 19, including:
stabilizing said antigen-conjugate-target-antibody capture molecule mixture by addition of glycerol thereto for reducing the incidence of non-specific protein aggregation.

25. An enzyme immunoassay process as recited in claim 19, wherein:
a buffering agent is mixed with said fluid specimen and said enzyme-conjugated antibody and is selected from the group consisting of phosphate, tris, glycine, citric acid and sodium acetate.

26. An enzyme immunoassay process as recited in claim 25, wherein:
said buffering agent ranges in molarity from about 0.001 M to about 0.3 M.

27. An enzyme immunoassay process as recited in claim 25, wherein:
said buffering agent ranges in pH from about pH 3.5 to about pH 10.

28. An enzyme immunoassay process as recited in claim 25, wherein:
said buffering agent contains blocking and coating proteins from a group consisting of bovine serum albumin, normal serum and gelatin and said buffering agent contains a surfactant.

29. An enzyme immunoassay process as recited in claim 28, wherein:
said surfactant is from a group consisting of Tween 20, Tween 80 and Triton.

30. An enzyme immunoassay process as recited in claim 19, wherein:
said filter membrane is composed of a group consisting of cellulose, fiberglass, filled cellulose, filled fiberglass capable of sustaining a predetermined electrostatic charge and having a pore size in the range of from about 0.2 microns to about 25 microns.

31. An enzyme immunoassay process as recited in claim 30, wherein:
said predetermined electrostatic charge is in the range of from strongly negatively charged to slightly positively charged.

32. An enzyme immunoassay process as recited in claim 19, wherein:
intensity of said color is compared visually to reference colors for qualitative and semi-quantitative interpretation.

33. An enzyme immunoassay process as recited in claim 32, wherein:
the intensity or fluoresence of said color is measured by density or reflectance photometry, yielding quantitative interpretation.

34. An enzyme immunoassay process as recited in claim 19, wherein:
said capture molecule and said target molecule are from a group consisting of avidin and biotin.

* * * * *